United States Patent [19]

Good et al.

[11] 4,004,143
[45] Jan. 18, 1977

[54] MEDICAL AND DENTAL LAMP

[75] Inventors: Palmer W. Good, Oak Brook; John P. Good, River Forest; Paul R. Hinz, Berkeley, all of Ill.

[73] Assignee: Good-Lite Company, Forest Park, Ill.

[22] Filed: June 27, 1975

[21] Appl. No.: 590,867

[52] U.S. Cl. .............................. 240/44.15; 240/47
[51] Int. Cl.² .......................................... A61B 1/06
[58] Field of Search ............. 240/41.15, 41.3, 41.4, 240/8.18, 41 R, 47

[56] References Cited

UNITED STATES PATENTS

| | | | |
|---|---|---|---|
| 2,026,156 | 12/1935 | Alexander et al. | 240/41.15 |
| 2,102,023 | 12/1937 | Overbury | 240/41.15 X |
| 2,224,225 | 12/1940 | Holroyd | 240/41.15 X |
| 2,309,104 | 1/1943 | Dircksen et al. | 240/41.3 |

*Primary Examiner*—Richard L. Moses
*Attorney, Agent, or Firm*—Burmeister, York, Palmatier, Hamby & Jones

[57] ABSTRACT

A lamp for illuminating the mouth of a patient which provides an oval pattern of adjustable size and intense illumination which generally conforms to the shape of a patient's mouth, and which is mounted at one end of a flexible tube or gooseneck. The lamp has an elongated filament positioned adjacent to a convex lens, the filament being located between the lens and the focal point of the lens and the distance between the filament and the lens being adjustable to vary the size of the pattern. The illuminating device is provided with a handle located between the flexible tube and the lamp, and the handle has an arm extending outwardly perpendicular to the axis of the filament and an electrical switch for controlling the flow of power to the lamp.

6 Claims, 5 Drawing Figures

U.S. Patent  Jan. 18, 1977  4,004,143
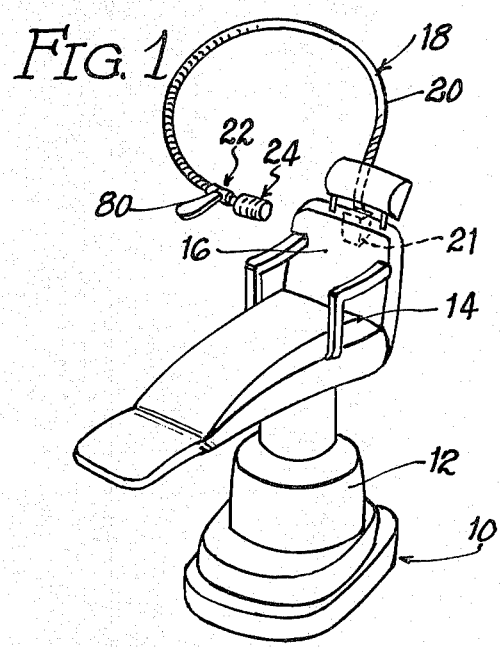
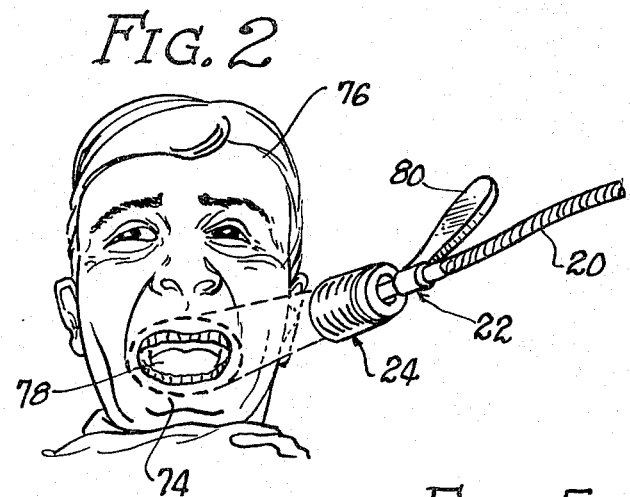
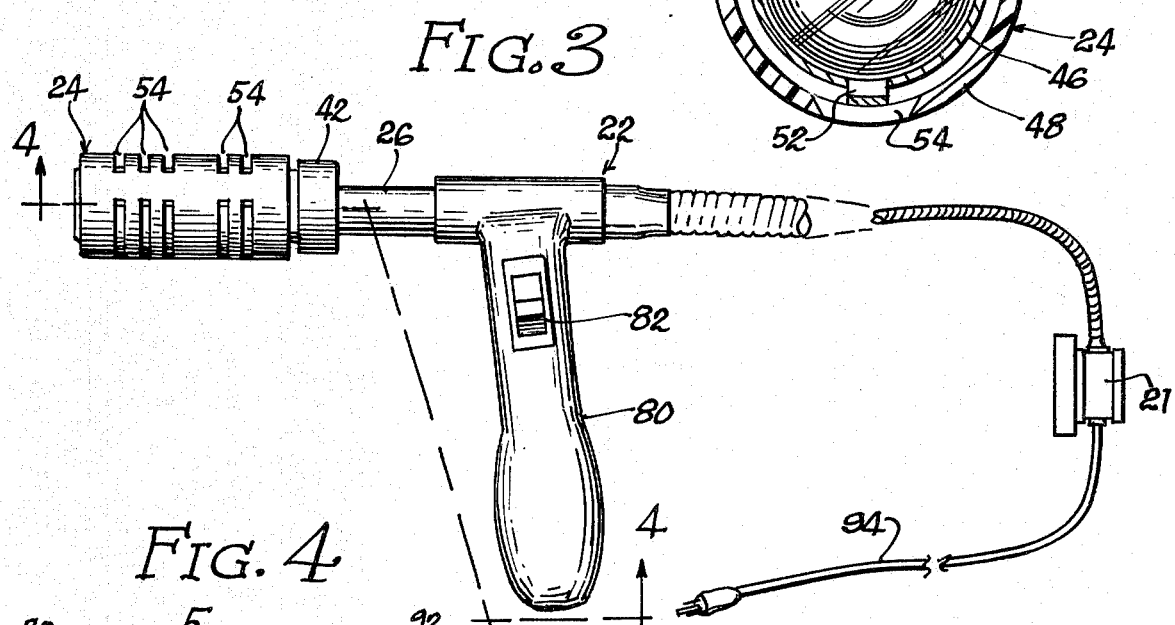
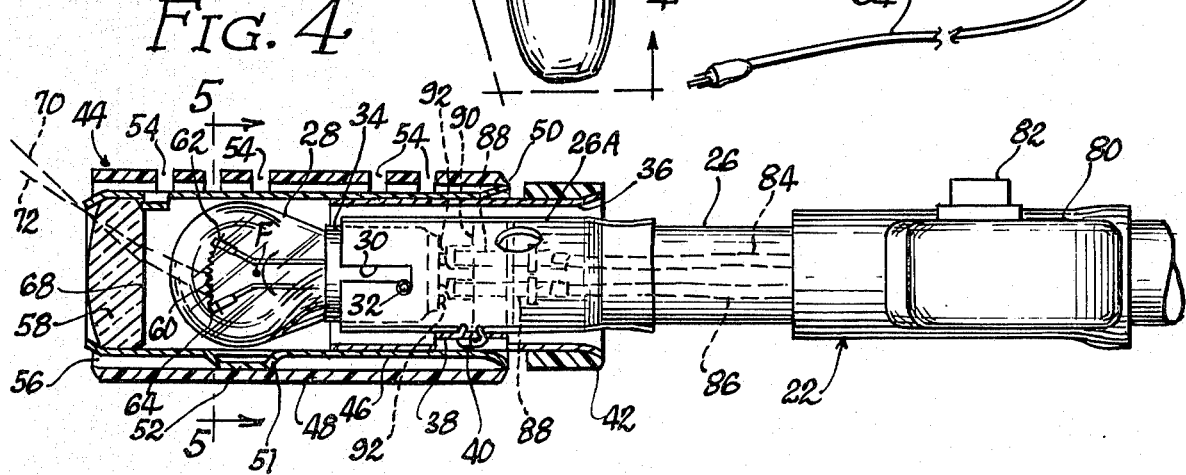

MEDICAL AND DENTAL LAMP

The present invention relates to devices for illuminating the mouths of patients, particularly human beings, such as are used by dentists or doctors.

Prior to the present invention, illuminating devices have been used principally by dentists to focus a remote high intensity light source on the mouth of a patient. Such light sources may be free standing or mounted on the back of a dental chair, but the sources are bulky, heavy, and expensive. Because of the bulk of the source, it must be positioned a relatively long distance from the mouth of the patient, such as three to four feet, in order to permit the dentist or doctor to examine or work on the mouth of the patient. Since the intensity of illumination varies inversely with the square of the distance from the light source, a relatively small amount of the illumination from such light sources actually penetrates into the mouth of the patient and is available to illuminate the areas of the mouth which the doctor or dentist desires to view. Additionally, the remoteness of such light sources complicates positioning the light source to view the particular portion of the mouth of the patient which the dentist or doctor desires to examine, and often the patient must move his head in order to accommodate the light source, rather than the doctor moving the light source to a position illuminating the spot that he desires.

It is therefore an object of the present invention to provide a device for illuminating the mouth of a patient which will place more light in the precise areas within the mouth that the physician or dentist desires to examine than prior light sources.

It is a further object of the present invention to provide a light source for illuminating the mouth of a patient which is more readily adjustable, and which can be adjusted by a physician or dentist while viewing the portions of the mouth which he desires to illuminate.

It is a further object of the present invention to provide a light source for a dentist or physician which is less bulky than prior light sources, less costly than the prior light sources, and more convenient to operate.

The present inventor has found that a light source with a flexible tube mounted at one end on a support means and carrying a handle at the other end with a lamp socket mounted on the handle and extending from the side of the handle opposite the flexible tube, the lamp socket carrying a lamp with an elongated thin filament mounted between two adjacent posts, and a convex lens mounted on the lamp socket on a plane parallel to the filament and displaced from the filament by a distance less than the focal length of the lens achieves the objects of the present invention. The lens is mounted within a tubular housing which is slidably mounted on the lamp socket, and translation of the housing with respect to the socket is effective to change the size of an oval light pattern to conform generally to the size of the mouth of the patient.

The present invention will be more fully described with reference to the accompanying drawings, in which:

FIG. 1 is a front elevational view of a light source constructed according to the teachings of the present invention and mounted on a dental chair;

FIG. 2 is a front elevational view of the light source of FIG. 1 illustrating the shape of the pattern of the light produced with respect to the shape of an open human mouth;

FIG. 3 is a top plan view, partly broken away, of a light source constructed according to the teachings of the present invention;

FIG. 4 is a sectional view taken along the line 4—4 of FIG. 3; and

FIG. 5 is a sectional view taken along the line 5—5 of FIG. 4.

FIG. 1 illustrates a light source constructed according to the present invention and mounted on a chair 10 adapted to be utilized by a physician or dentist for examining the mouth of a patient. The light source may be mounted on other supporting structures, but the combination of a chair and light source is a convenient unitary structure. The chair has a base 12 which is adapted to rest upon the floor of the doctor or dentist's office and which carries a seat 14. The seat 14 has a back 16, and a lamp 18 is mounted on the back 16 of the chair 10.

The lamp has a flexible tube 20, which also may be referred to as a gooseneck, mounted at one end on a transformer housing 21, and the housing 21 is mounted on the back 16 of the seat 14. A handle 22 is mounted on the end of the flexible tube 20 opposite the housing 21, and an illumination unit 24 is carried by the handle 22.

The illumination unit 24 has a hollow cylindrical rod 26 which extends from the handle 22 and has an extension rod 26A forming a socket for a lamp 28. The extension 26A is provided with L-shaped slots 30 at its end opposite the handle 22 to receive and accommodate outwardly extending pins 32 from the base 34 of the lamp 28. The extension 26A is surrounded by a hollow cylindrical shell 36 which is spaced from the extension to permit the circulation of air between the two elements. The shell 36 is provided with inwardly extending projections 38 which are secured on the extension 26A by screws 40.

An outwardly extending cylindrical collar 42 is disposed on the shell 36 and its end confronting the handle 22. A lens assembly 44 is slidably disposed on the external surface of the shell 36 and may be translated into abutment and away from the collar 52. The lens assembly 44 has a hollow cylindrical inner sleeve 46 and a hollow cylindrical outer sleeve 48 disposed about and spaced from the inner sleeve at the end adjacent to the collar 42 by an outwardly flaring portion 50. The inner sleeve 46 is provided with a plurality of pairs of elongated slits 52 which form outwardly bent strips 51 disposed generally parallel to the axis of the sleeve, and the outer sleeve 48 is provided with elongated slots 54 disposed an axes generally normal to the axis of the sleeve 48. As a result of this construction, air heated by the lamp 28 may circulate through the annular gap between the extension 26A and the shell 36, through the slits 52 in the inner sleeve 46, the slots 54 in the outer sleeve 48, and an annular opening 56 between the ends of the inner sleeve 46 and the outer sleeve 48 opposite the flaring portion 50.

A lens 58 is mounted on the end of the inner sleeve 46 of the lens assembly 44 confronting the lamp 28. The lens 58 is a convex lens, and FIG. 4 illustrates the location of one of the focal points F for the lens 58. The lamp 28 is provided with an elongated incandescent filament 60 mounted on a pair of posts 62 and 64 within a glass envelope 66, and the filament 60 is disposed on an axis traversing the axis between the focal points of the lens 58 and located between the plane of the lens, designated 68, and the focal point F. Accordingly, light rays emanating from the filament 60 parallel to the axis of the focal points will diverge from the lens 58, thereby producing a field of substantially uniform illumination. Since the lens assembly 44 is translatable on the shell 36, the lens 58 may be moved with respect to the filament 60, thereby changing the size of the uniform field of illumination. The field of illumination, however, will remain larger than the diameter of the lens 58 as long as the filament 60 is located between the lens 58 and the focal point F.

The filament 60 constitutes a line source of illumination, and since the filament is disposed between the focal point F and the convex lens 58, the filament 60 produces a divergent field of illumination in which the end of the inner sleeve 46 forms a circular stop. As viewed in FIG. 4, illumination emanating from the lower end of the filament 60 and within the upper stop follows the ray designated 70, while illumination emanating from the center of the filament just within the peripheral stop follows the ray 72. Since the filament 60 is essentially a point source in the plane perpendicular to that shown in FIG. 4, the ray 72 represents the outer limit of the field of illumination in the plane perpendicular to that of FIG. 4, while the ray 70 represents the outer edge of the field of illumination in the plane of FIG. 4. Accordingly, an oval shaped field of illumination results, this field of illumination being illustrated at 74 in FIG. 2. It will be noted that FIG. 2 also illustrates the head 76 of a man, and the field of illumination 74 substantially coincides with the open mouth 78 of the man 76.

It is desirable for the physician or dentist utilizing the light source to be able to readily position the light source with respect to the mouth 78. This is particularly important, since the light source will be positioned at a relatively short distance from the mouth, of the order of one foot. Accordingly, the handle 22 is provided with an outwardly extending arm 80 which may be gripped by the physician or dentist in positioning the light source. The arm 80 is disposed normal to the axis of elongation of the filament 60, so that rotation of the light source by means of rotating the handle 22 rotates the major axis of the oval field of illumination 74 to bring it into alignment with the major axis of the open mouth 78 being observed.

The flexible tube or gooseneck 20 permits rotation of the handle 22 and attached illumination unit 24, and also permits displacement of the handle 22 and illumination unit 24 with respect to the mouth 78. In addition, the flexible tube 20, or gooseneck, holds the illumination unit 24 in position once the physician or dentist has properly positioned it.

A rocker switch 82 is mounted in the arm 80 of the handle 22 and electrical wires 84 and 86 extend from a pair of pins 88 extending through an insulating disc 90. The disc 90 is mounted within the extension 26A to position the pins 88 into abutment with the terminals 92 of the lamp 28. The wires 84 and 86 extend through the flexible tube 20 to the transformer housing 21, the wire 84 including the switch 82 in its circuit. The transformer housing 21 contains a transformer for converting power received from transmission lines through a conventional cord 94 to the potential required for the lamp 28.

The fact that the oval pattern of illumination may be changed in size to conform generally to the open mouth of a patient functions in cooperation with the flexible tube 20. The flexible tube 20 may be adjusted to position the illumination unit 24 at that distance from the mouth 78 of the patient which will achieve the desired access for the physician or dentist, and the size of the oval illumination field may then be adjusted to maximize the light emitted from the lamp 28 at the particular location within the mouth of the patient. Since the intensity of illumination varies inversely with the distance between the light source and the point under observation, it is obviously desirable to position the illumination unit 24 as close to the patient's mouth as consistent with the doctor or dentist's space requirements. Further, the smaller the field of illumination, the more intense the illumination in the field. Accordingly, the physician's lamp described above permits the physician to maximize illumination from a relatively small and low powered lamp at a precise location.

Those skilled in the art will devise many uses and modifications for the physician's lamp described above. For example, the light source may be mounted directly to a portion of the building structure in which it is used, as well as on a chair as illustrated. It is therefore intended that the scope of the present invention be not limited by the foregoing specification, but rather only by the appended claims.

The invention claimed is:

1. A medical and dental lamp adapted to illuminate the mouth of patients comprising in combination; a flexible tube adapted to be mounted on a supporting means at one end, a handle having a tubular portion mounted on the flexible tube at the other end thereof and extending therefrom, and a light source for projecting an oval pattern including a lamp holder mounted on the handle and extending from the side thereof opposite the flexible tube, a lamp mounted on the lamp holder having an elongated thin filament, a hollow elongated sleeve, means for slidably mounting the sleeve on the handle for translation along an axis normal to the axis of the elongated filament, said means including tubular shell slidably disposed within the sleeve and mounted on the handle, said shell being spaced from the handle to provide an air passage, and said sleeve having openings therein confronting the lamp for circulation of air through the passage, over the lamp, and through the openings in the sleeve, the lamp being disposed within and directly confronting the sleeve, a convex lens mounted on the sleeve in a plane normal to the axis of the sleeve, translation of said sleeve changing the distance between the lens and the filament.

2. A medical and dental lamp adapted to illuminate the mouth of a patient comprising the combination of claim 1 wherein the supporting means comprises a chair.

3. A medical and dental lamp adapted to illuminate the mouth of a patient comprising the combination of claim 1 wherein the handle is provided with an arm extending outwardly from the lamp holder, said arm being at a fixed angle with respect to the axis of the filament of the lamp.

4. A medical and dental lamp adapted to illuminate the mouth of a patient comprising the combination of claim 3 including a source of electrical energy disposed at the end of the flexible tube opposite the lamp, an electrical switch mounted on the handle, and electrical wires electrically connected to the lamp at the holder, to the electrical switch, and to the source of electrical energy, said wires extending through the flexible tube.

5. A medical and dental lamp adapted to illuminate the mouth of the patient comprising the combination of claim 1 wherein the means for slidably mounting the sleeve on the handle includes a collar mounted on the outer surface of the shell at the end thereof opposite the lamp, said collar being aligned with the sleeve and forming a stop against translation of the sleeve.

6. A medical and dental lamp adapted to illuminate the mouth of the patient comprising the combination of claim 1 in combination with an outer hollow tubular member mounted on the sleeve confronting and spaced from the exterior surface thereof, said member being provided with apertures to permit the circulation of air.

* * * * *